United States Patent
Amon et al.

[11] Patent Number: 5,735,896
[45] Date of Patent: Apr. 7, 1998

[54] BIOCOMPATIBLE PROSTHESIS

[75] Inventors: Michael Amon, Dormitz; Armin Bolz, Erlangen, both of Germany

[73] Assignee: Biotronik, Berlin, Germany

[21] Appl. No.: 417,966

[22] Filed: Apr. 6, 1995

[30] Foreign Application Priority Data

Aug. 15, 1994 [DE] Germany ............... 44 29 380.1

[51] Int. Cl.$^6$ ................. A61F 2/02; A61F 2/04
[52] U.S. Cl. ........................... 623/11; 623/1
[58] Field of Search ............... 623/1, 2, 11, 12, 623/16, 18

[56] References Cited

U.S. PATENT DOCUMENTS

| | | |
|---|---|---|
| 4,656,083 | 4/1987 | Hoffman et al. |
| 4,824,690 | 4/1989 | Heinecke et al. |
| 5,034,265 | 7/1991 | Hoffman et al. |
| 5,080,668 | 1/1992 | Bolz et al. ............... 623/2 |
| 5,163,955 | 11/1992 | Love et al. ............... 623/2 |
| 5,238,866 | 8/1993 | Bolz et al. |

FOREIGN PATENT DOCUMENTS

| | | |
|---|---|---|
| 0371908 | 6/1990 | European Pat. Off. |
| 0 472 941 | 7/1991 | European Pat. Off. |
| 0 601 804 | 6/1994 | European Pat. Off. |
| 43 01 188 | 7/1994 | Germany. |
| 57-155365 | 9/1982 | Japan. |
| 2165266 | 4/1986 | United Kingdom. |

OTHER PUBLICATIONS

Boltz, A. et al, "New Coating Materials for Artificial Heart Valves", Images of the Twenty-First Century, Proceedings of the Annual International Conference of the IEEE Engineering in Medicine and Biology Society (Cat. No. 89CH2770-6), Seattle, WA, 9–12 Nov. 1989, Bd. 11, 1989, New York, NY, IEE, pps. 164–166.

*Primary Examiner*—Debra S. Brittingham
*Attorney, Agent, or Firm*—Spencer & Frank

[57] ABSTRACT

A method of producing a biocompatible prosthesis based on a substrate made essentially of metal or ceramic. The substrate is placed into a reactor chamber of a cathodic vapor deposition arrangement and the chamber is evacuated to a predetermined pressure. A predetermined, negative bias voltage is then applied to the substrate and the substrate is surface treated by adding an etching gas to the reactor chamber, at a predetermined, first flow rate and coupling in a high frequency power with a first, predetermined power density for ionic etching for a first, predetermined period of time. The surface treated substrate is separated from the negative bias voltage and a semiconductor cover layer is chemical vapor-phase deposited on the substrate by adding to the reactor chamber a multi-component mixture of process gases containing a semiconductor element in bound format a second, predetermined flow rate and coupling-in of HF power with a predetermined, second power density, for a second, predetermined time period.

4 Claims, 5 Drawing Sheets

BIOCOMPATIBLE PROSTHESIS

CROSS-REFERENCE TO RELATED APPLICATIONS

This application claims the right of priority with respect German application P 44 29 380.1 filed in Germany on Aug. 15, 1994, the disclosure of which is incorporated herein by reference.

BACKGROUND OF THE INVENTION

The invention relates to a method of producing a biocompatible prosthesis and, in particular, a non-collapsing, intravascular prosthesis, such as a stent, made essentially of either metal or ceramic and to a prosthesis made by the method.

Cardiovascular implants can be used in the human body particularly as heart valve prostheses or vascular prostheses or pacemaker electrodes. The surface of the implant must possess high blood compatibility (antithrombogenity).

Generic implants as disclosed in European application EP 0 371 908 B1 and having a coating of, for example, silicon carbide (SIC), particularly with an amorphous layer structure, have for the most part achieved satisfactory parameters with regard to blood compatibility. These coatings, which possess high quality, can be produced in a simple manner by a plasma-enhanced vapor-phase deposition (PECVD) method, as disclosed in detail in U.S. Pat. No. 5,238,866.

The formation of the coating on the substrate is effected at relatively high temperatures of around 250° C., possibly up to 350° C., so that structural tensions which limit the adherence of the coating arise during cooling.

In connection with percutaneous transluminal coronary angioplasty (PTCCA), which has been practiced in the last few years and has been intensively advanced systematically, the use of intravascularly expandable, non-collapsing vascular prostheses or stents, has achieved significance.

In an implant that is subjected to considerable material deformation during use, it is necessary that the implant have good plastic ductility with a suitable yield point to permit sufficient, uniformelongation to take place. This requires an extraordinarily strong adherence between the substrate and the biocompatible coating. The adherence must prevent a detachment of the coating, even when relatively severe deformations of the substrate occur.

SUMMARY OF THE INVENTION

It is an object of the invention to provide a method of producing a vascular prosthesis of the generic type mentioned at the outset which has a surface layer that is compatible with blood and has very good adherence to the substrate material, particularly high-grade steel.

The above and other objects are accomplished in accordance with the invention by the provision of a method of producing a biocompatible prosthesis based on a prefabricated substrate comprised essentially of either metal or ceramic, the method comprising: placing the substrate into a reactor chamber of a cathodic vapor deposition arrangement and evacuating the chamber to a predetermined pressure; surface treating the substrate by applying a predetermined, negative bias voltage to the substrate, and adding an etching gas, at a predetermined, first flow rate and coupling in a high frequency (HF) power, with a first, predetermined power density, into the reactor chamber for ionic etching a surface of the substrate for a first, predetermined period of time; separating the surface-treated substrate from the negative bias voltage; and chemical vapor-phase depositing a semiconductor cover layer on the surface of the substrate by adding a multi-component mixture of process gases containing a semiconductor element in bound form at a second, predetermined flow rate and coupling-in of HF power, with a predetermined, second power density, into the reactor chamber for a second, predetermined time period.

As a result of the method of the invention, the substrate surface is thoroughly cleansed of adsorbates, particularly hydrocarbons and oxides, prior to the application of the biocompatible coating. Further an augmentation of defects in the substrate surface is effected in order to create favorable preconditions for a stable chemical and physical bonding of the applied coating at a boundary layer. Finally, the invention utilizes an arrangement that is necessary anyway for layer formation.

According to a another aspect of the invention, a further increase in adhesion can be attained in an advantageous manner in that an intermediate step is performed after the surface treatment of the prefabricated prosthesis. This step involves applying a predetermined, second, negative bias voltage to the surface-treated substrate, supplying a process gas containing the semiconductor material in bound form at a predetermined flow rate, and coupling HF power having a predetermined power density into the sputter reactor for a given time period in order to perform a plasma-enhanced deposition of a thin bonding agent layer that contains the semiconductor element.

The semiconductor element is preferably silicon, and the semiconductor cover layer contains silicon carbide, or is essentially composed of silicon carbide. In particular, the cover layer is embodied as an amorphous layer. Its thickness is preferably a few hundred nm, particularly approximately 400 nm.

An inert gas, particularly argon, nitrogen or carbon tetrachloride, is preferably used as the etching gas in the step of surface treatment, whereas in the step of vapor-phase deposition, the mixture of process gases preferably includes monosilane.

When a silicon-bonding layer is used, the bonding agent layer essentially comprises silicon. The process gas used in forming the bonding agent layer can also preferably be monosilane, and the thickness of the bonding agent layer is preferably a few nm, and more preferably about 3 to 5 nm.

A prefabricated prosthesis, or stent, preferably of high-grade steel, but alternatively of a titanium or tantalum alloy or platinum/iridium, is used as the substrate.

An important factor for good adhesion of the coating on the substrate is that the temperature of the prefabricated prosthesis be kept constant, preferably at about 250° C., during the entire process. This prevents the formation of layer tensions during the process. For this purpose, during the transition to the chemical vapor-phase deposition and execution of this step, the prosthesis is heated by essentially inertia-free substrate heating, because in this phase essentially no more heating takes place through ion bombardment.

To prevent a deposit of residual gases on the surface of the prosthesis between process steps, the separation of the substrate from the negative bias voltage advantageously takes place without interrupting the coupling-in of the HF power, i.e. the plasma is maintained in the reactor chamber.

Due to a continuous change of the process gas composition over a given period of time, the bonding agent layer and the semiconductor cover layer can be formed so as to blend at an increasing distance from the surface of the prefabricated substrate, and not possess a distinctive boundary surface, with the component of the semiconductor element, for example elementary Si, being removed.

In another aspect of the invention, there is provided a biocompatible prosthesis comprising a prefabricated substrate made essentially of metal or ceramic and having a semiconductor cover layer covering its surface, wherein there is a boundary surface formed between the surface of the substrate and the semiconductor cover layer whose microstructure is characterized by reciprocal bumps and dents and an alloy-like chemical structure.

Both the substrate material that is near the surface and the boundary surface are essentially free from oxygen and/or hydrocarbons, which is partially responsible for the good adhesiveness of the cover layer.

In a preferred embodiment, the boundary layer is formed between the metal or ceramic surface of the prefabricated substrate and the bonding agent layer of semiconductor material.

Other advantages, features and modifications of the invention will be appreciated from the following detailed description of the invention when considered in conjunction with the accompanying drawings.

DETAILED DESCRIPTION OF THE PREFERRED EMBODIMENTS

Figure 1:
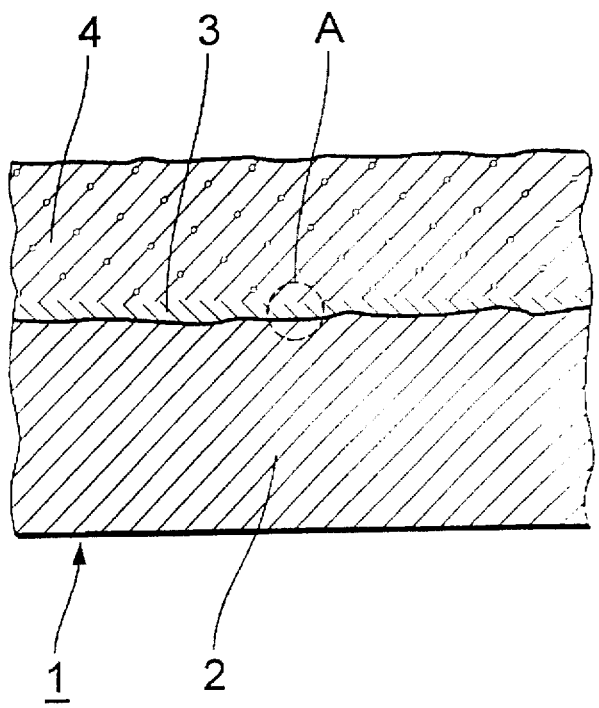
FIG. 1 is a schematic, cross-sectional representation of the layer structure in an embodiment of the prosthesis produced according to the invention.

Referring to FIG. 1, there is shown a schematic, cross-sectional representation of the layer structure of an anti-thrombogenic prosthesis, in this case a stent 1, made according to the invention, for use in the therapy of coronary vascular stenoses. FIG. 1 is not to scale with respect to the layer thickness ratios.

Stent 1 comprises a substrate 2, for example of 316L high-grade steel, on which there is formed an intermediate layer 3 of amorphous silicon a—Si having a thickness of about 3–5 nm and, on this layer, there is formed a cover layer 4 of amorphous, n-doped silicon carbide a—SiC:H having a thickness of about 400 nm. Intermediate layer 3 and cover layer 4 are not separated from each other by a defined boundary surface, but rather blend into one another.

Figure 1A:
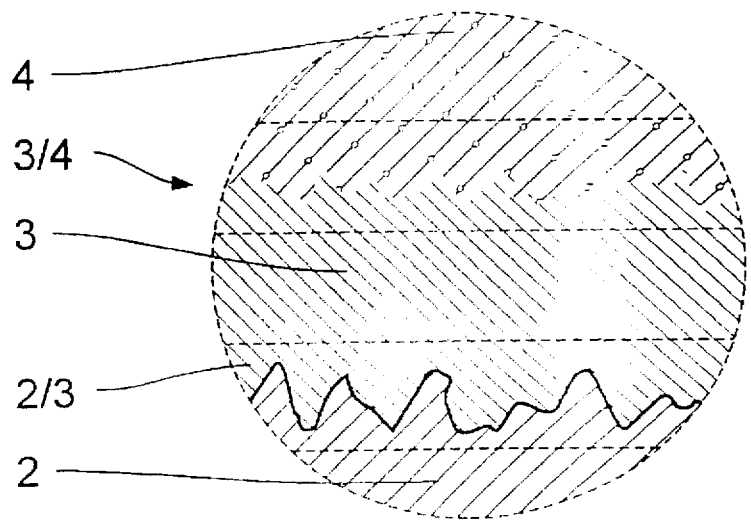
FIG. 1a is an enlarged, representation of the circled area in FIG. 1.

FIG. 1a shows an enlargement of the circled area A in FIG. 1. It can be seen here that the boundary surface between substrate 2 and intermediate or bonding agent layer 3 is not even, but has a severely fissured microstructure, i.e. there is a boundary surface 2/3 (shown between dashed lines in FIG. 1a) having interlocked bumps and dents of adjacent materials that are fused in an alloy-like structure. Boundary surface 3/4 between bonding agent layer 3 and cover layer 4 has a similar microstructure, in which the carbon component increases from the bottom to the top.

It is significant for the function of bonding agent layer 3 that there be practically no foreign atoms, particularly oxide or hydrocarbon deposits, on the substrate material in the region of the bonding agent layer, including its boundary surfaces.

Figure 2:
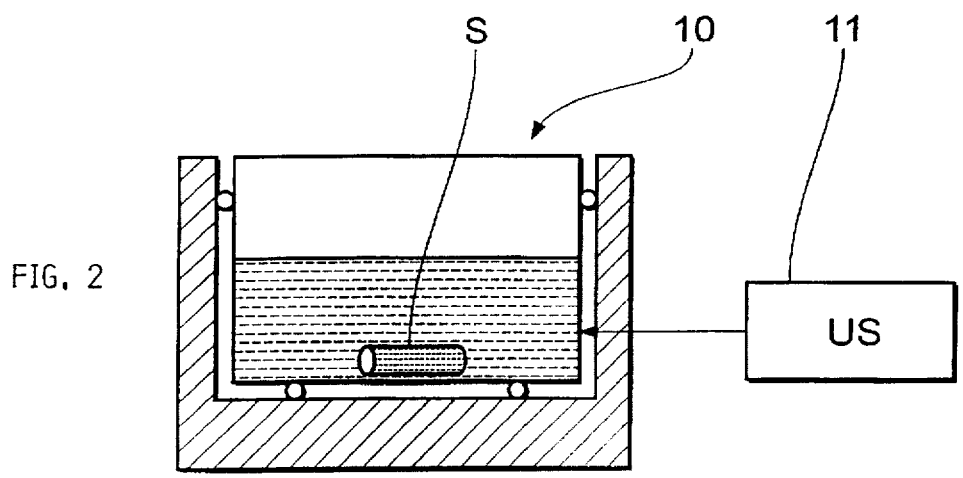
FIG. 2 is a schematic cross-section showing a first stage of the method of the invention in which the prefabricated substrate is given an ultrasound bath.
Figure 2A:
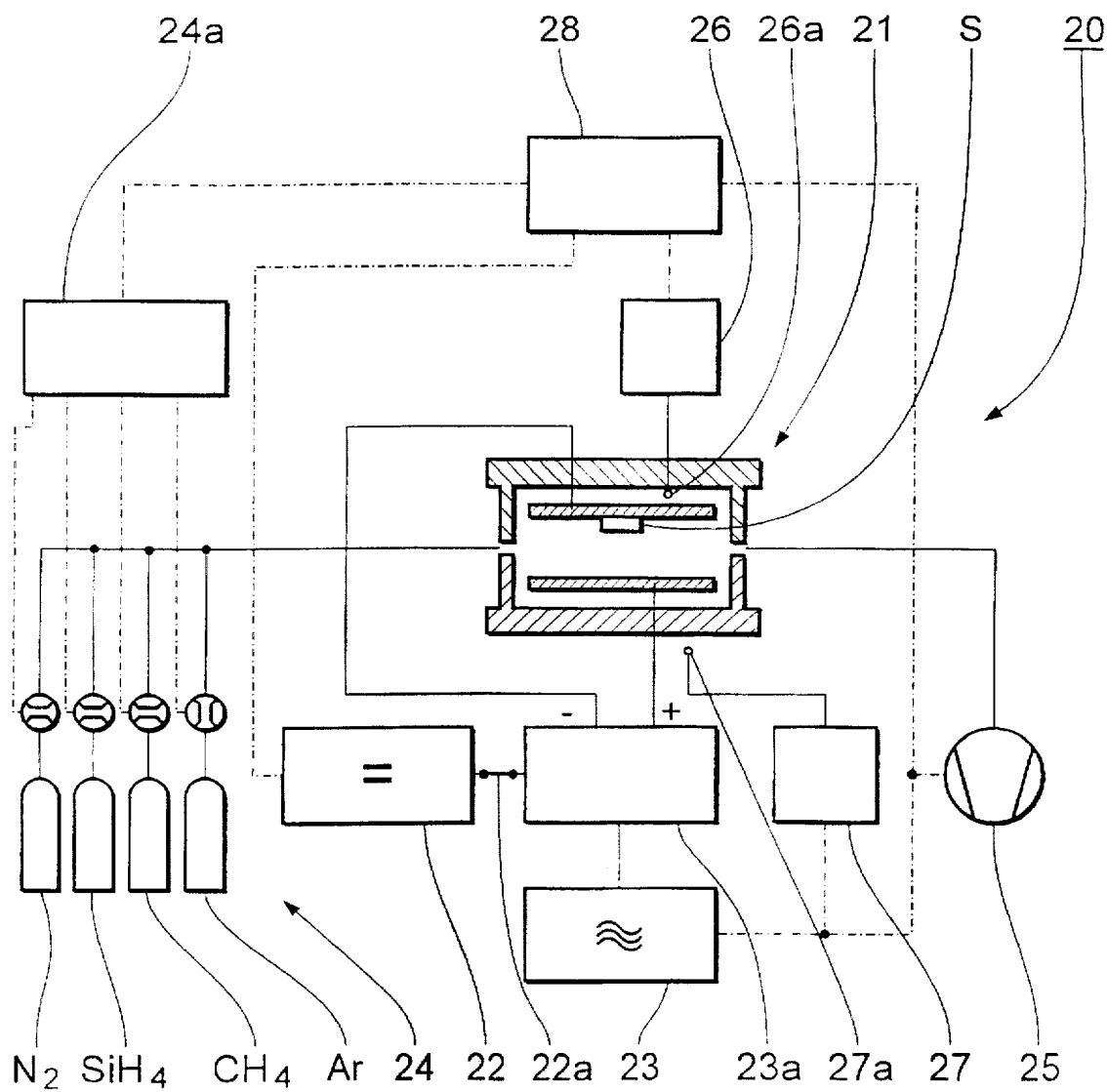
FIGS. 2a through 2c are schematic representations including block circuit diagrams used to explain further steps of the method of the invention.
Figure 2B:
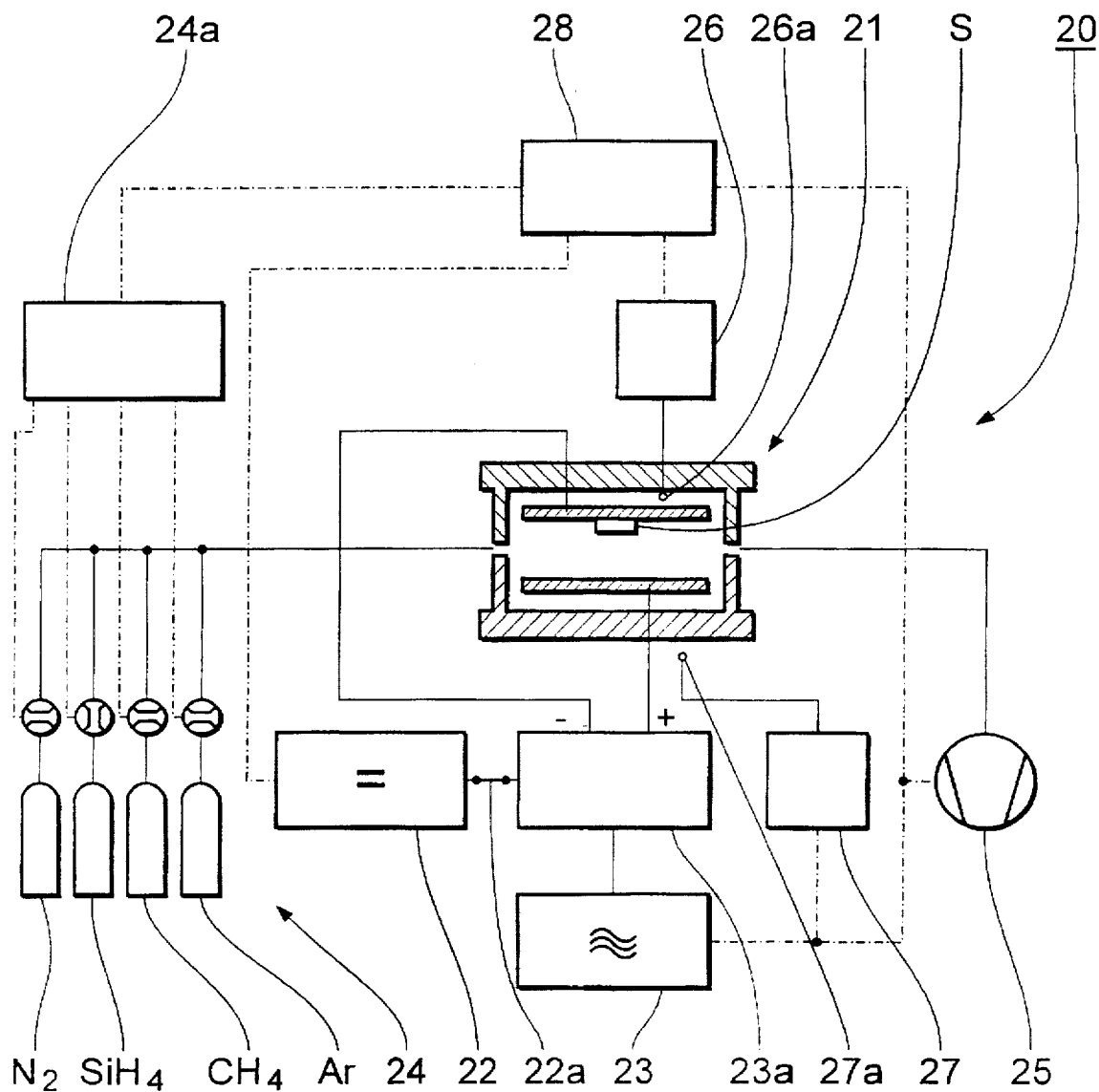
Figure 2C:
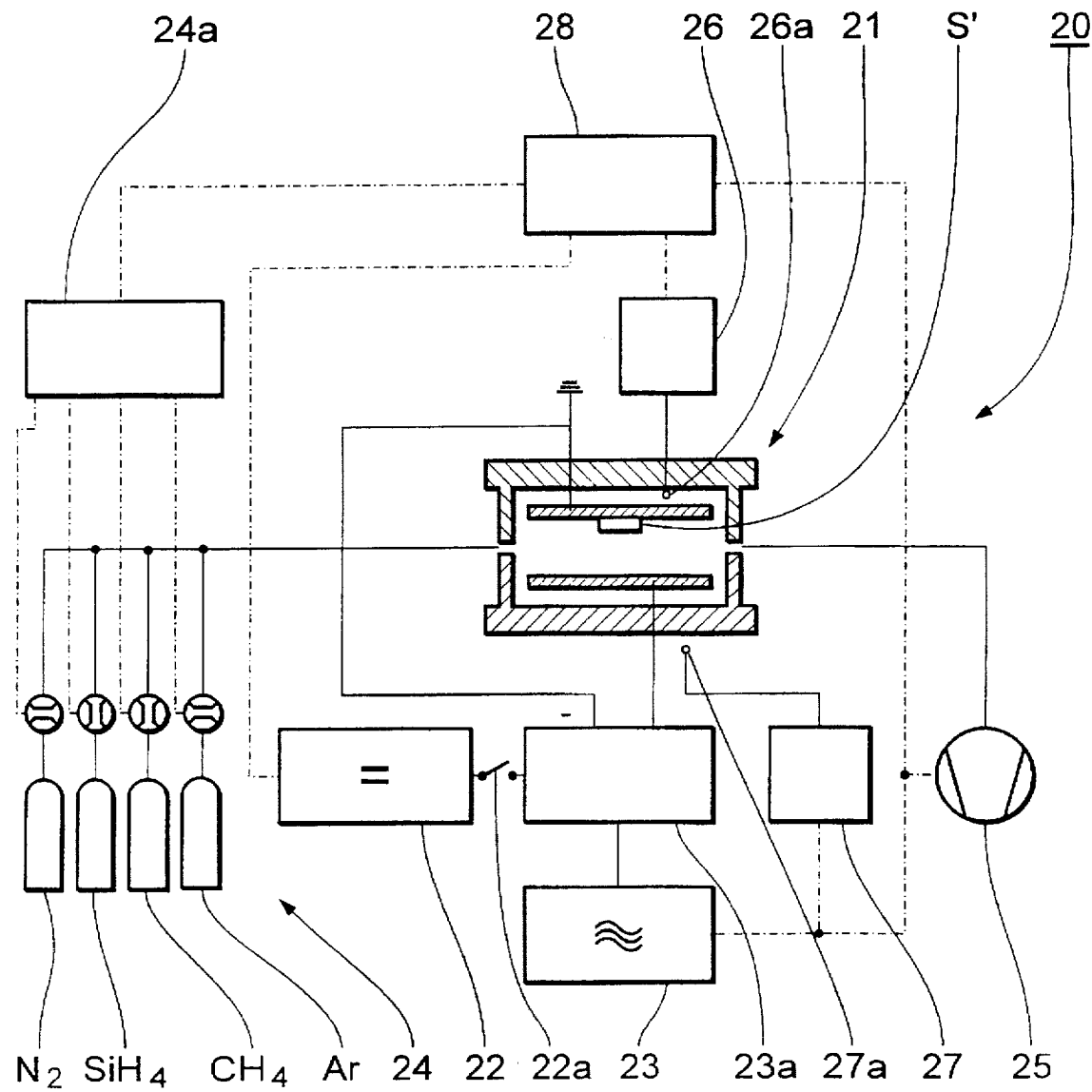

FIGS. 2a through 2c are schematic representations for clarification of the essential steps of the method for applying the biocompatible, adhesive coating to a prosthesis, such as a stent, according to an embodiment of the invention.

FIG. 2 illustrates a first method stage (a), in which a prefabricated substrate S of 316L high-grade steel and having the shape of the prosthesis, or stent, is first cleaned in an isopropanol bath 10 by means of ultrasound supplied by a conventional ultrasound transmitter 11.

Referring to FIG. 2a, in a second stage (b), substrate S is subjected to a plasma enhanced ionic etching or a reactive ionic etching treatment in a reactor chamber 21 of a parallel-plate reactor arrangement 20. In addition to the actual reactor chamber 21, reactor arrangement 20 includes a d.c. voltage source 22 that has a cut-off switch 22a; an HF transmitter 23 that has a matching network 23a; a gas supply 24 that has a flow-regulating and measuring unit 24a; a vacuum-generating system 25; a pressure-measuring unit 26 that has an absolute pressure sensor 26a; a temperature measurement and control unit 27 that has a pyroelectric T-detector 27a; and a process-control unit 28.

In a practical embodiment of arrangement 20, temperature measurement and control unit 27 includes a group of halogen lamps (not shown in the drawings) aimed at substrate S to effect a nearly inertia-free additional heating of the substrate.

In stage (b), reactor chamber 21 is initially evacuated to a pressure of less than $10^{-8}$ bar, and substrate S is preheated to 250° C. for approximately 10 minutes.

Following this step, only the valve of the Ar (argon) container is opened in gas supply 24, whereas the valves of the other gas containers are closed. Argon is admitted into reactor chamber 21 through gas supply 24. With a gas flow of up to approximately 40 sccm, a pressure in a range of $2\times10^{-6}$ to $10^{-5}$ bar is established.

In FIGS. 2a and 2b, cut-off switch 22a of d.c. voltage supply 22 is closed thereby applying a negative bias voltage (in a range of approximately 500 to approximately 1500 volts, preferably 1000 volts) to substrate S. Substrate S is thus cathodically polarized in this method stage, in which the bias voltage is established according to the parameters of the arrangement and the desired end product. In addition, HF transmitter 23 couples into reactor chamber 21 HF power with power density in a range of 0.16 W/cm² for a period of 10 to 15 minutes. During this period the temperature of substrate S is kept substantially constant at about 250° C.

In this phase, ionic etching of the surface of substrate S takes place under the conditions disclosed above. In the process, deposits, particularly of hydrocarbons, are effectively removed, and an increase in the defect density on the surface occurs. This creates advantageous preconditions for the formation of stable chemical bonds between substrate S and a layer applied directly thereafter.

The next method stage (c) is likewise performed in reactor arrangement 20, as shown schematically in FIG. 2b. In this stage, the valve of the argon container is closed, and the valve of the $SiH_4$ container is open. The gas flow is at 40 sccm, and the process gas pressure is at $4\times10^{-5}$ bar. Substrate S is further acted upon by a negative bias voltage that may be in the same range as in stage (b) or preferably even above it (at approximately 2000 V). The temperature is again kept substan-tially constant at about 250° C.

In this stage the surface of substrate S is subjected to a high-energy bombardment with silicon. This bombardment leads to a further structuring of the surface and, simultaneously, to the deposit of amorphous silicon (a—Si). After a process length of a few (approximately five) minutes, this forms a 3 to 5 nm thick layer that is closely interlocked with the substrate surface. Interdiffusion processes along the crystal boundaries in this layer lead to the formation of chemical bonds between components of the substrate and the silicon.

A fourth and essential stage (d) of the method is likewise performed in reactor arrangement 20, as can be seen in FIG. 2c. In this stage, the valves of the monosilane ($SiH_4$) and methane ($CH_4$) containers in gas supply 24 are both open. The individual flow rates for ($SiH_4$) and ($CH_4$), which in practice are additionally mixed with a small amount of phosphine, are controlled individually by process control unit 28 to correspond to the desired elementary proportions of Si and C in the layer to be deposited. Advantageous settings of the gas flows have been found to be 35.5 sccm for $SiH_4$, 3.53 sccm for $CH_4$ and 37.2 sccm for $PH_3$. The process gas pressure is $8 \times 10^{-5}$ bar, and the substrate temperature is again 250° C. The substrate temperature can only be reached with the additional halogen heating in this method stage, because no more warming due to ion bombardment takes place.

In stage (d), cut-off switch 22a is open so that a d.c. voltage is no longer applied to the electrodes and the electrode that receives the substrate is grounded. Thus, in this stage (d), the substrate is not acted upon by a d.c. bias voltage. Rather, stage (d) of the method is performed with capacitively coupled-in HF power supplied by HF stage 23 at, for example 13.56 MHz with a power density of 0.16 W/$cm^2$.

Over the course of this latter stage of the method, known as plasma-enhanced, chemical vapor-deposition (PECVD), a layer having a thickness of a few hundred, preferably 400 nm, and made of amorphous silicon carbide (a—SiC) is deposited on the high-grade-steel substrate S (more precisely, on the thin a-Si layer covering the substrate) in an $SiH_4/CH_4$ atmosphere with a gas composition that has been predetermined by the valves of gas supply 24. Since the supply of the monosilane does not take place abruptly when the corresponding valve is opened, the layer of pure Si and the SiC layer blend as the C component is gradually added. This completes the biocompatible stent.

The biocompatible SiC layer has outstanding adhesiveness that is expressed in a significantly increased critical strength in a conventional scratch test.

Figure 3A:
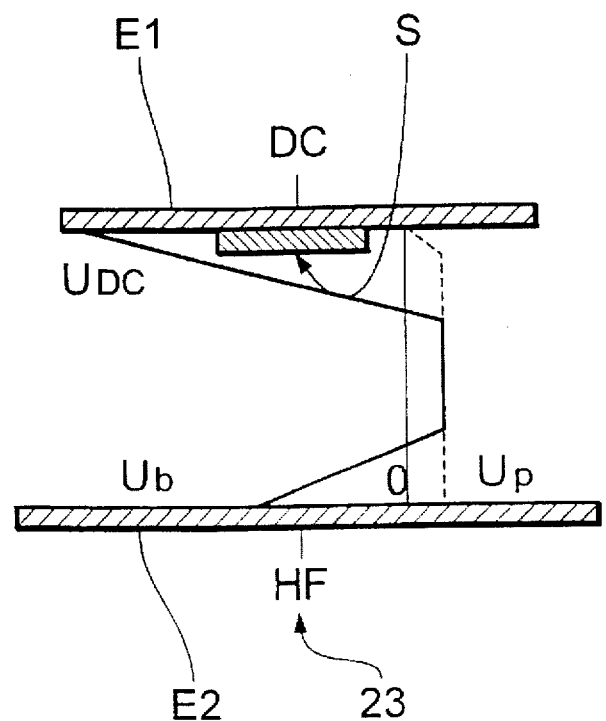
FIGS. 3a and 3b are schematic representations of the potential curve between the electrodes of the device in different steps, respectively.
Figure 3B:
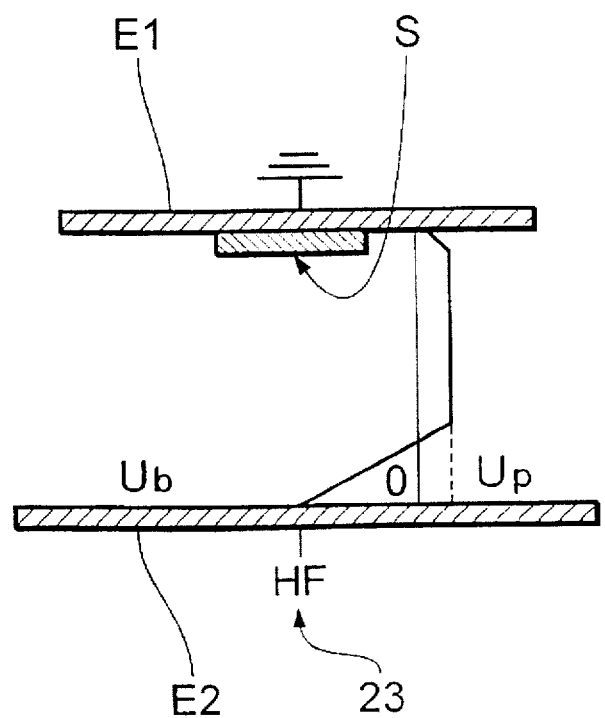

FIGS. 3a and 3b are schematic representations of the potential curve between the electrodes of the device in step (b) according to FIGS. 2a and step (d) according to FIG. 2c. An upper electrode E supports the substrate. The HF power from HF stage 23 is capacitively coupled into a lower electrode E2. In stages (b) and (c), a high negative bias voltage is applied to upper electrode E1 as shown in FIG. 3a. In stage (d), E1 is grounded as shown in FIG. 3b.

The process gas particles are very effectively ionized by the potential curve illustrated in FIG. 3a, and high ionic currents that lead to an effective removal of impurities are accelerated onto the surface of substrate S. In the transition to the coating of cover layer 4, according to FIG. 3b, only the d.c. voltage is cut off, in which case the plasma is retained and no interruptions of the process occur that would disadvantageously lead to a deposit of residual gases on the surface, and thus to a deterioration of the adhesiveness.

The implementation of the illustrated potential curves requires the use of filters that prevent, on the one hand, a coupling of the HF into the d.c. voltage source and, on the other hand, a mutual influence between d.c. voltage source 22 and HF generator 23. These are included in matching network 23a.

The illustrated shape and position of the components of reactor arrangement 20, as well as the position of substrate S in this arrangement, are to be understood solely in the sense of a purely schematic representation. The arrangement can be modified in numerous ways. In a different structure, altered power densities and gas flows that may also be essential for the creation of an optimum layer must be established.

The above-described method can also be employed, with appropriately varied materials and method parameters, with other implantation materials, and with other biocompatible layers. In particular, a similar coating of titanium alloys (e.g. TiAl5Fe2,5), tantalum, platinum/iridium, pyrolytic carbon or oxide ceramic (e.g. $ZrO_2$) with a—SiC is possible. In principle, other semiconductive coating materials having suitable band gaps can be used, in which case the selection of the process gases is, of course, a function of the chemical composition of the layer to be produced, but is also to be regarded as being basically known for a certain layer composition. However, according to the investigations conducted by the inventors, SiC is to be regarded as an advantageous material in numerous aspects.

The step of applying the intermediate layer can also be omitted. The embodiment of method stages (b) and (d) according to FIGS. 2a and 2c is to be considered essential to the invention.

The invention is not limited in its embodiment to the above-disclosed, preferred embodiment. Rather, a number of variations are conceivable which utilize the illustrated solution, even in fundamentally different types of configurations.

The invention has been described in detail with respect to preferred embodiments, and it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

What is claimed is:

1. A biocompatible prosthesis, comprising:
   a prefabricated substrate comprised of one of a metallic and a ceramic material;
   a cover layer including a semiconductor material covering a surface of the substrate; and
   a boundary layer having a microstructure including reciprocal bumps and dents formed between the surface of the substrate and the cover layer said bumps and dents interlocking said substrate and said cover layer.

2. The biocompatible prosthesis according to claim 1, further comprising a semiconductor bending agent layer comprised of the same semiconductor material as the cover layer and being disposed between the boundary layer and the cover layer.

3. The biocompatible prosthesis according to claim 1, wherein the boundary layer has an alloy-type chemical structure.

4. The biocompatible prosthesis according to claim 1, wherein the surface of the substrate and the boundary layer are essentially free from oxygen and hydrocarbons.

* * * * *

UNITED STATES PATENT AND TRADEMARK OFFICE
CERTIFICATE OF CORRECTION

PATENT NO : 5,735,896
DATED : April 7, 1998
INVENTOR(S): Michael AMON et al.

It is certified that error appears in the above-identified patent and that said Letters Patent are hereby corrected as shown below:

On the title page, change line [73], to read --BIOTRONIK Mess-und Therapiegerate GbmH & Co. Ingenieurburo Berlin, Berlin, Germany--.

Signed and Sealed this

Tenth Day of April, 2001

*Attest:*

NICHOLAS P. GODICI

*Attesting Officer*     *Acting Director of the United States Patent and Trademark Office*